(12) United States Patent
Leichner et al.

(10) Patent No.: US 11,337,891 B2
(45) Date of Patent: May 24, 2022

(54) RESERVOIR FOR STORING A LIQUID MEDICAMENT AND METHOD OF PRODUCING A RESERVOIR

(71) Applicant: Roche Diabetes Care, Inc., Indianapolis, IN (US)

(72) Inventors: Wilhelm Leichner, Mannheim (DE); Hans List, Hesseneck-Kailbach (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 534 days.

(21) Appl. No.: 16/346,678

(22) PCT Filed: Nov. 21, 2017

(86) PCT No.: PCT/EP2017/079860
§ 371 (c)(1),
(2) Date: May 1, 2019

(87) PCT Pub. No.: WO2018/095886
PCT Pub. Date: May 31, 2018

(65) Prior Publication Data
US 2019/0275216 A1    Sep. 12, 2019

(30) Foreign Application Priority Data
Nov. 23, 2016    (EP) .................................... 16200141

(51) Int. Cl.
*A61J 1/14*    (2006.01)
*A61M 5/148*    (2006.01)
(Continued)

(52) U.S. Cl.
CPC ............ *A61J 1/1475* (2013.01); *A61M 1/602* (2021.05); *A61M 5/148* (2013.01);
(Continued)

(58) Field of Classification Search
CPC .. A61J 1/1475; A61J 1/145; A61J 1/10; A61J 1/1493; A61M 2205/7527; A61M 2205/126; A61M 5/148
See application file for complete search history.

(56) References Cited

U.S. PATENT DOCUMENTS 5,988,422 A  * 11/1999 Vai .................... C12M 23/14
                                                              220/62.22
2005/0277882 A1    12/2005 Kriesel
(Continued)

FOREIGN PATENT DOCUMENTS

EP    2 196 231    6/2010
EP    2 319 477    5/2011
(Continued)

*Primary Examiner* — Jenna Zhang
(74) *Attorney, Agent, or Firm* — Woodard, Emhardt, Henry, Reeves & Wagner, LLP

(57) ABSTRACT

The invention concerns a reservoir (1) for storing a liquid medicament. The reservoir (1) comprises a flexible container (10) which includes one folding layer (12), wherein the folding layer (12) includes a seam (13) which provides for a sealing of the flexible container (1). The reservoir comprises a rigid part (20) which is connected to the flexible container (10) and which includes a support (25) extending into the flexible container (10) and which includes one or more ports (21, 22) providing fluidic access to the flexible container (10). The reservoir comprises a porous hydrophilic membrane (26) which is connected to the support (25) of the rigid part (20). The invention further concerns a method for producing of a reservoir (1). The method comprises: providing a flexible tube (30) and a movable opening device (40) located inside the flexible tube (30), moving (S1) the moveable opening device (40) inside the flexible tube (30) by a distance in a longitudinal direction of the flexible tube (30), providing a rigid part (20), and bonding (S2) the
(Continued)

flexible tube (30) to the rigid part (20) and providing a folding layer (12) included in the flexible container (10).

16 Claims, 3 Drawing Sheets

(51) Int. Cl.
    *A61M 5/14*     (2006.01)
    *A61M 1/00*     (2006.01)

(52) U.S. Cl.
    CPC ..... *A61M 5/1413* (2013.01); *A61M 2205/123* (2013.01); *A61M 2205/126* (2013.01); *A61M 2205/7527* (2013.01); *A61M 2209/045* (2013.01)

(56) References Cited

U.S. PATENT DOCUMENTS

| | | | |
|---|---|---|---|
| 2008/0060467 A1 | 3/2008 | Manwaring et al. | |
| 2009/0236338 A1* | 9/2009 | Elton | B65D 75/26 |
| | | | 220/62.22 |
| 2010/0130957 A1* | 5/2010 | Smisson, III | A61M 1/3627 |
| | | | 604/408 |
| 2013/0253439 A1* | 9/2013 | Wyss | A61M 5/14248 |
| | | | 604/246 |
| 2019/0256270 A1* | 8/2019 | Bazin | A61J 1/10 |
| 2019/0274923 A1* | 9/2019 | Bazin | B65B 3/045 |
| 2019/0307642 A1* | 10/2019 | Schlack | A61J 1/1493 |

FOREIGN PATENT DOCUMENTS

| | | |
|---|---|---|
| EP | 2 455 128 | 5/2012 |
| EP | 2 229 927 | 6/2013 |

\* cited by examiner though, possible also other cross section designs include to the flexible container such as, for example, at least one of 2 and 100 and other values.

RESERVOIR FOR STORING A LIQUID MEDICAMENT AND METHOD OF PRODUCING A RESERVOIR

FIELD OF THE INVENTION

The present invention relates to a reservoir for storing a liquid medicament. The present invention relates further to a method of producing a reservoir for storing a liquid medicament. The present invention further relates to a method for filling a reservoir for storing a liquid medicament. The present invention further relates to a method for delivering an amount of a liquid medicament from a reservoir having stored the liquid medicament. The invention further relates to a medical pump for the automated administration of a liquid medicament.

BACKGROUND ART

In connection with the administration of liquid medicaments, for example in pain therapies, in treatment of diabetes, etc., infusion pump devices, such as insulin pumps, are used. The pump devices have arranged containers for storing the liquid medicament. These devices can be carried by a patient on the body. The containers can have a disposable design for reasons of sterility, contamination-prevention, etc. The containers can have a reusable design enabling to be filled and re-filled by a user, for example in case of medicaments that are not available in pre-filled containers, wherein a larger choice of sources of medicaments is provided, in case of medicaments having limited stability when stored in plastic containers, etc. The containers can have a rigid or a flexible design. Rigid containers can comprise a cylinder having arranged a plunger that is controlled by a motor for dosing the liquid medicament. The precision of such systems is relatively low and prone to malfunction because of air bubbles, change of position, etc. In case of flexible containers, the liquid medicament is administered using a small pump. Flexible containers have the advantage of a smaller volume surplus, reduced manufacturing costs, etc.

EP2229927 discloses a flexible container for storing a liquid medicament. The container comprises two wall sheets of a flexible material that are sealed together. The container comprises a storage compartment for the liquid medicament and an access opening on one of the wall sheets. The container comprises an insert part that is arranged between the two wall sheets with positive locking and that fluidly connects the storage compartment and the access opening. The wall sheets are sealingly connected along a peripheral sealing rim. Instead of two wall sheets, one single folded sheet can be used. The container may include a connection device for use in an infusion pump device. The connection device may comprise a degassing membrane.

EP2455126 discloses a container for storing a medical or pharmaceutical liquid. The container comprises a storage compartment for storing the liquid. The storage compartment comprises an inlet opening for filling the storage compartment and an outlet opening for discharging liquid out of the storage compartment. A hydrophilic membrane is arranged within the storage compartment, which is gas-tight in a wet condition and which at least covers the outlet opening and which contacts the liquid stored in the storage compartment. The container comprises two wall parts, wherein a first wall part is realized by a rigid wall part and a second wall part is realized by a flexible wall sheet. The two wall parts are joined together for establishing a gas and liquid tight bonding.

US20100130957 describes a collapsible fluid reservoir that may be expanded during use and collapsed to lie substantially flat when not in use. The fluid reservoir can be used during certain surgical procedures, such as cardiologic procedures, to temporarily hold biological fluids such as blood. The collapsible fluid reservoir can include a non-rigid container having an open proximal end and a sealed distal end opposite the proximal end defining a cavity therein, wherein the distal end includes a fluid outlet port. The collapsible fluid reservoir can include a rigid cap affixed to the proximal end and including a fluid inlet port. The cross-sectional shape of the proximal end can be circular, ovular, or polygonal.

DISCLOSURE OF THE INVENTION

It is an object of the present invention to provide a reservoir and a method of producing a reservoir, which do not have at least some of the disadvantages of the prior art. In particular, it is an object of the present invention to provide a reservoir and a method of producing a reservoir, wherein the reservoir makes efficient use of available space. In particular, it is an object of the present invention to provide a reservoir and a method of producing a reservoir, wherein the reservoir is robust. In particular, it is an object of the present invention to provide a reservoir and a method of producing a reservoir, wherein the reservoir is inexpensive.

According to the present invention, these objects are achieved through the features of the independent claims. In addition, further advantageous embodiments follow from the dependent claims and the description.

According to the present invention, the above-mentioned objects are particularly achieved by a reservoir for storing a liquid medicament, which reservoir comprises: a flexible container which includes one folding layer, wherein the folding layer includes a seam which provides for a sealing of the flexible container. The reservoir comprises a rigid part which is connected to the flexible container and which includes a support extending into the flexible container and which includes one or more ports providing fluidic access to the flexible container. The reservoir comprises a porous hydrophilic membrane which is connected to the support of the rigid part. The rigid part provides a robust design and for example enables installation in and connection with a liquid pump, while the flexible container enables that available space is efficiently used. The porous hydrophilic membrane provides a robust design and prevents that air bubbles are administered together or instead of the liquid medicament. Production of the reservoir requires few parts and can be inexpensive. In an embodiment, the liquid medicament includes insulin. In a dry state, the porous hydrophilic membrane is permeable to air, such that air can pass the porous hydrophilic membrane when the flexible container contains air. The air can be sucked out of the flexible container before filling the flexible container with the liquid medicament. In a wet state, as soon as the porous hydrophilic membrane is in contact with the liquid medicament, the porous hydrophilic membrane is air-impermeable, thereby preventing that air bubbles are administered together or instead of the liquid medicament.

In an embodiment, the flexible container includes a cross section with a rectangular design. A rectangular design makes efficient use of available space.

In an embodiment, the flexible container includes a section of a foil tube. A section of a foil tube is available at low costs. The size of the flexible container, namely the available volume for storing the liquid medicament, can be adapted to requirements by selecting a section of the foil tube having a predefined length.

In an embodiment, the folding layer provides that walls of the flexible container exhibit a curved surface. The curved surface may provide for a robust design. The curved surface may simplify unfolding or folding of the flexible container when filling the reservoir with a liquid medicament or when delivering an amount of the liquid medicament from the reservoir. The curved surface may vary considerably as relates shape, dimensions, etc. For example, the curved surface may have the shape of a conoid, a paraboloid, etc.

The seam, which is included in the folding layer, provides an inexpensive sealing of the flexible container.

In an embodiment, the folding layer and the rigid part are arranged on opposite sides of the flexible container. The reservoir has a robust design while the rigid part provides for robust installation and connection with a medical pump and the other side of the reservoir provides for robust unfolding and folding of the flexible container.

In an embodiment, the flexible container is bonded to the rigid part. Bonding may include heat sealing, ultrasonic welding, high-frequency inductive welding, gluing, etc. The reservoir has a robust design and the flexible container is firmly connected to the rigid part.

Because the rigid part includes a support extending into the flexible container and supporting the porous hydrophilic membrane, the reservoir has a robust design and the porous hydrophilic membrane is firmly arranged in the reservoir.

Because the rigid part includes one or more ports providing fluidic access to the flexible container, the reservoir has a robust design and provides for fluidic connection with a medical device such as a medical pump.

In an embodiment the rigid part includes one or more mounting parts for mounting the reservoir to a medical device. In some embodiments, the one or more mounting parts includes one or more pins. The reservoir has a robust design and provides for firm mounting to a medical device such as a medical pump.

In an embodiment, the rigid part includes one or more pins for mounting the reservoir to a medical device. The reservoir has a robust design and provides for firm mounting to a medical device such as a medical pump.

The invention further relates to a method for producing of a reservoir as described in the present specification. The method comprises: providing a flexible tube and a movable opening device located inside the flexible tube, moving the moveable opening device inside the flexible tube by a distance in a longitudinal direction of the flexible tube, providing a rigid part, and bonding the flexible tube to the rigid part and providing a folding layer included in the flexible container. The flexible tube can be provided in a large quantity enabling inexpensive production of the reservoir. The flexible tube can be provided in the form of a roll. The method enables production of inexpensive reservoirs having a robust design. By varying the distance the moveable opening device is moved inside the flexible tube, the volume of the flexible container of the reservoir can be varied and easily adapted to predefined requirements.

In an embodiment, the foil tube and the rigid part are provided having a rectangular cross section enabling bonding of the flexible tube to the rigid part in a kitty corner manner. Accordingly, the flexible container of the reservoir has a cubic design thereby making efficient use of available space, wherein the bonding in a kitty corner manner provides for a robust design. In accordance to Merriam-Webster, the term "kitty corner" defines that the arrangement is in a diagonal or oblique position, such as in the example of a house standing kitty-corner across a square. "kitty-corner" means "diagonally opposite" and applies to the way how the rigid part and the foil tube fit together especially at the corners of their rectangular shapes.

The invention further relates to a method for filling a reservoir as described in the present specification. The method comprises: actuating a fill device connected to the reservoir for filling the reservoir via the one or more ports at least partly with the liquid medicament thereby unfolding the flexible container. For example, the fill device can pump the liquid medicament into the reservoir. The flexible container unfolds in accordance to the amount of the filled liquid medicament. In a variant, the method comprises: actuating a fill device connected to the reservoir thereby unfolding the flexible container and having stored the liquid medicament for filling the reservoir at least partly with the liquid medicament.

The invention further relates to a method for delivering a liquid medicament from a reservoir as described in the present specification. The method comprises: actuating a delivery device connected to the reservoir for at least a partial delivery via the one or more ports of the liquid medicament stored in the reservoir thereby folding the flexible container. The liquid medicament is delivered via the one or more ports to a further medical device, such as for example, a medical pump. For example, the delivery device can suck the liquid medicament from the reservoir. The flexible container folds in accordance to the amount of the delivered liquid medicament. In a variant the method comprises: actuating a delivery device connected to the reservoir for at least a partial delivery of the liquid medicament stored in the reservoir thereby folding the flexible container.

The invention further relates to a medical pump for the automated administration of a liquid medicament, wherein the medical pump comprises a reservoir as described in the pre sent specification.

BRIEF DESCRIPTION OF THE DRAWINGS

The herein described invention will be more fully understood from the detailed description given herein below and the accompanying drawings which should not be considered limiting to the invention described in the appended claims. The drawings are illustrating schematically:

MODE(S) FOR CARRYING OUT THE INVENTION

Figure 1:
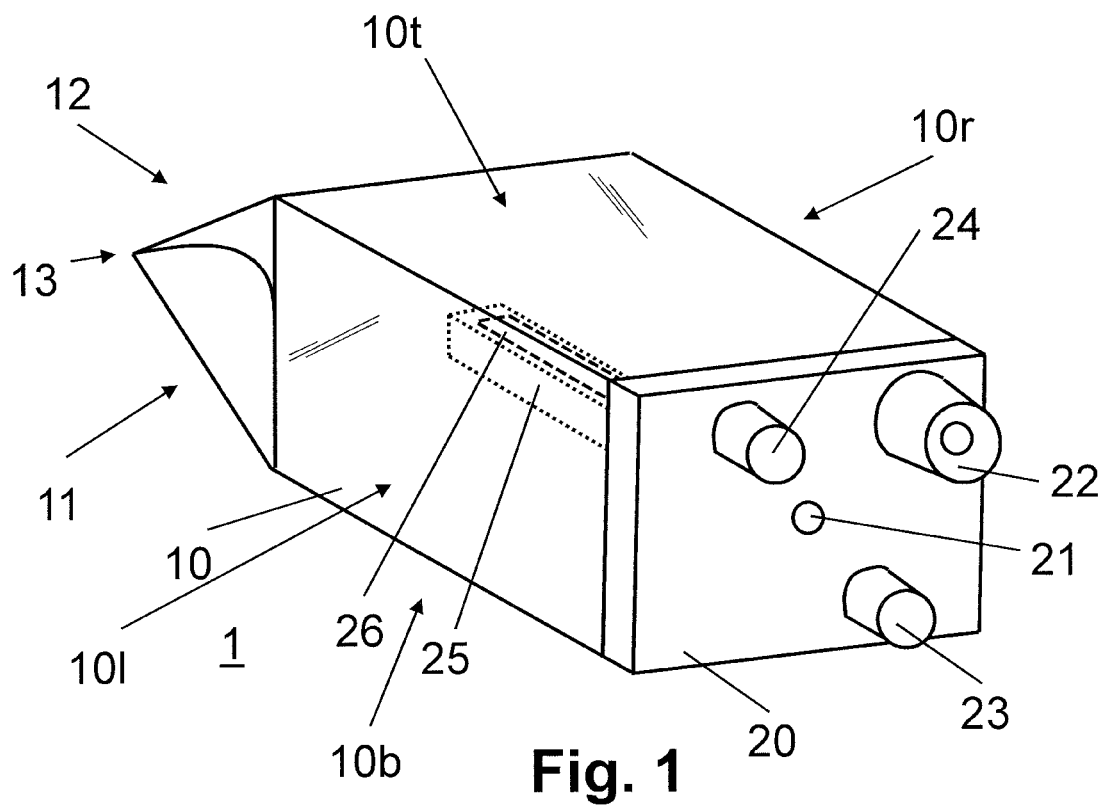
FIG. 1 a reservoir for storing a liquid medicament.
Figure 2:
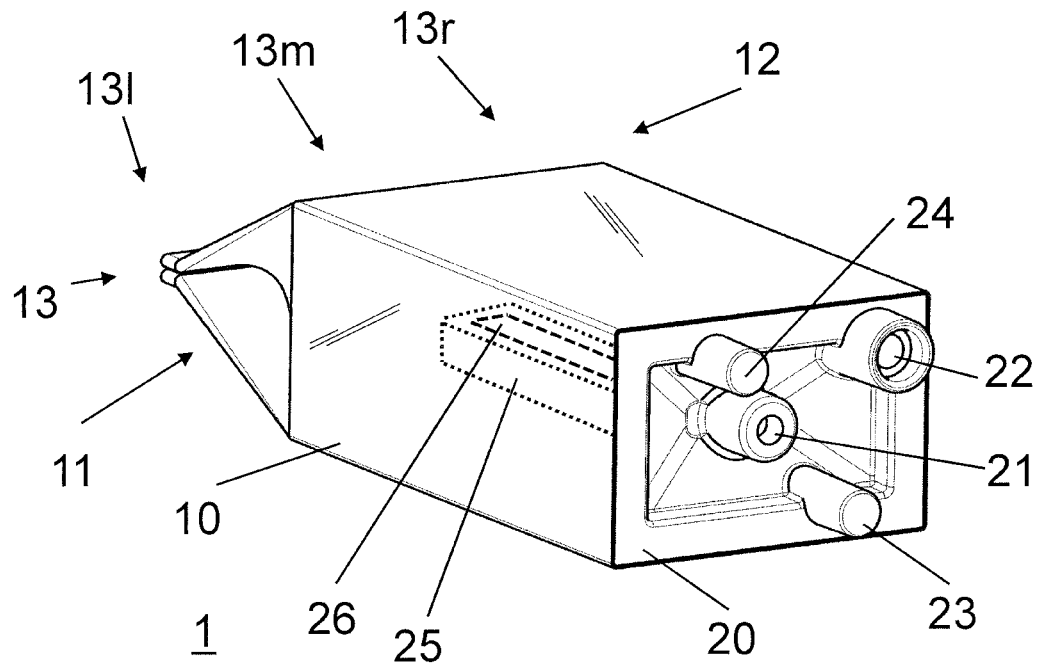
FIG. 2 a rendered view of the reservoir for storing a liquid medicament.

FIG. 1 illustrates schematically a reservoir 1 for storing a liquid medicament, for example for storing a liquid medicament such as insulin. FIG. 2 illustrates a rendered view of the reservoir 1 for storing a liquid medicament. FIG. 1 and FIG. 2 correspond to each other.

In order to improve clarity of the illustrations, some reference signs are included only in FIG. 1 or only in FIG. 2.

The reservoir 1 comprises a flexible container 10. The flexible container 10 may include a foil, such as a plastic foil. The flexible container 10 has essentially the form of a rectangular cuboid having a top wall 10*t*, a bottom wall 10*b*, a left wall 10*l* and a right wall 10*r*, as indicated with arrows in FIG. 1. The denomination of the top wall 10*t*, the bottom wall 10*b*, the left wall 10*l* and the right wall 10*r* is in accordance to their positions illustrated in FIG. 1 and in FIG. 2.

The flexible container 10 is connected to a rigid part 20. The rigid part 20 has essentially the form of a rectangular cuboid. The form of the rigid part 20 is adapted to the form of the flexible container 10. For example, a foil included in the flexible container 10 may be bonded to the rigid part 20 in a kitty corner manner.

The flexible container 10 includes a folding layer 12. The folding layer 12 and the rigid part 20 are arranged on opposite sides of the flexible container 10.

Figure 3:
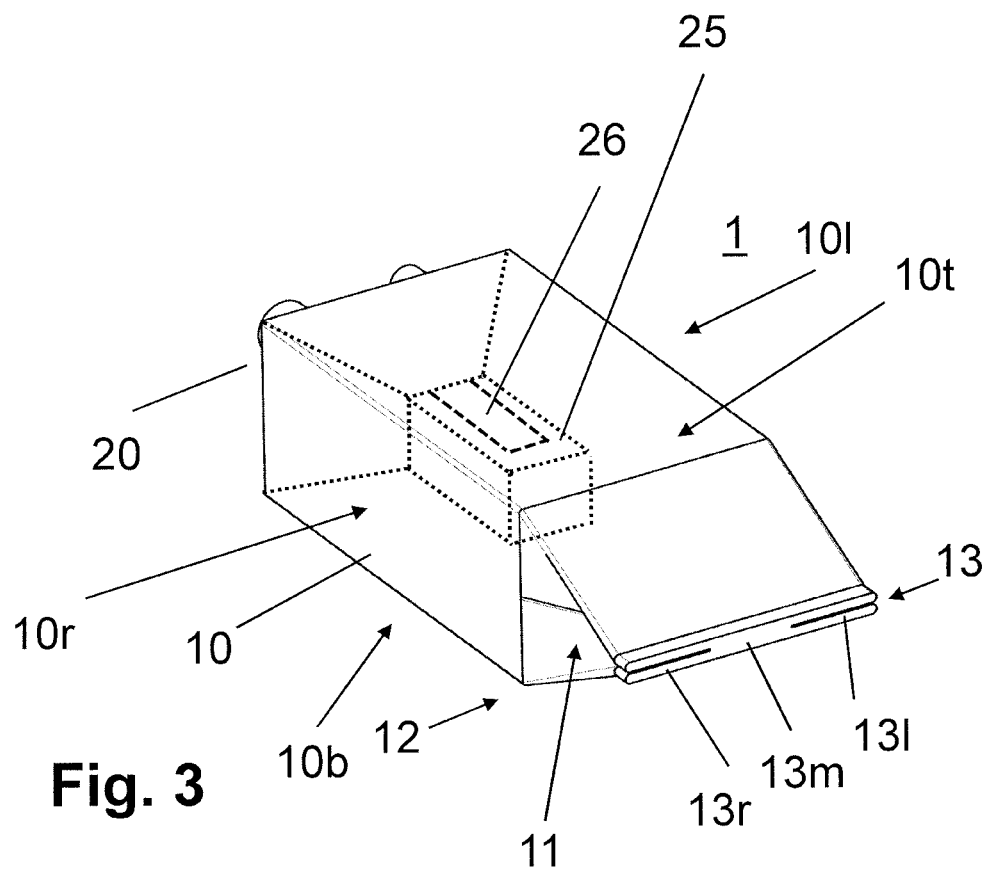
FIG. 3 a different rendered view of the reservoir for storing a liquid medicament.

Following the flexible container 10 in direction to the folding layer 12, the top wall 10*t*, the bottom wall 10*b*, the left wall 10*l* and the right wall 10*r* continue into the folding layer 12. The folding layer 12 includes a seam 13 which provides for a sealing of the flexible container 10. As illustrated in FIG. 2 and FIG. 3 (which will be described in more detail below), the seam 13 extends in a horizontal direction essentially from a plane defined by the left wall 10*l* to a plane defined by the right wall 10*r*. The seam 13 is arranged with respect to a plane defined by the bottom wall 10*b* on about a height which is the middle between the top wall 10*t* and the bottom wall 10*b*. A middle section 13*m* of the seam 13 connects together parts of the top wall 10*t* and the bottom wall 10*b*. A left section 13*l* of the seam 13 connects together parts of the left wall 10*l*, the top wall 10*t* and the bottom wall 10*b*. A right section 13*r* of the seam 13 connects together parts of the right wall 10*r*, the top wall 10*t* and the bottom wall 10*b*.

As illustrated in FIG. 1 and FIG. 2, the folding layer 12 has the shape of a gable roof that is turned by 90 degrees, wherein the left gable, which faces a plane defined by the left wall 10*l*, and the right gable, which faces a plane defined by the right wall 10*r*, exhibit a curved surface 11. The shape of the curved surface 11 depends on geometries, material properties, fill level, etc. of the flexible container 10. FIG. 1 and FIG. 2 illustrate that the curved surface 11 is included in the folding layer 12, wherein the other parts of the flexible container 10 do not include the curved surface 11. However, depending on the geometries, material properties, fill level, etc., the curved surface 11 may extend from the seam 13 to the rigid part 20.

As illustrated in FIG. 1 and FIG. 2, the rigid part 20 includes one or more ports 21, 22. The ports 21, 22 provide fluidic access to the flexible container 10. The port with reference sign 21 may be designed for delivering an amount of the liquid medicament from the reservoir 1. The port with reference sign 22 may be designed for filling the reservoir 1 with the liquid medicament. The port with reference sign 22 designed for filling the reservoir 1 may include a flange for attaching a filling device. The port with reference sign 22 designed for filling the reservoir 1 may include a septum.

As illustrated in FIG. 1 and FIG. 2, the rigid part 20 includes one or more pins 23, 24. The pins 23, 24 provide for mounting the reservoir 1 to a medical device such as a medical pump.

Unfolding of the flexible container 10 occurs while filling the reservoir 1 with a liquid medicament. Folding of the flexible container 10 occurs while delivering an amount of the liquid medicament from the reservoir 1.

As illustrated in FIG. 1 and FIG. 2, the rigid part includes a support 25 which extends into the flexible container 10 and which supports a porous hydrophilic membrane 26. The porous hydrophilic membrane 26 avoids the entry of air during folding and unfolding once it is wetted by the liquid medicament.

The flexible container 10 provides for efficient use of available space. Unfolding the flexible container 10 prevents the liquid medicament from swashing and deterioration. The rigid part 20 provides for a stable mounting of the reservoir 1 to a medical device such as a medical pump. The rigid part 20 provides for fluidic access to the flexible container 10, which enables filling of the flexible container 10 with a liquid medicament and delivery of the liquid medicament from the flexible container 10. Folding and unfolding of the flexible container 10 occurs with respect to the stable rigid part 20. The rigid part 20 provides for a stable mounting of the porous hydrophilic membrane 26.

FIG. 3 illustrates a different rendered view of the reservoir 1 for storing a liquid medicament. With respect to FIG. 1 and FIG. 2, the reservoir 1 is rotated about 180 degrees about a vertical axis.

As illustrated in FIG. 3, the reservoir 1 includes a flexible container 10 and a rigid part 20. The flexible container 10 includes a folding layer 12. The rigid part 20 includes a support 25 extending into the flexible container 10 and supporting an porous hydrophilic membrane 26. The flexible container 10 includes a top wall 10*t*, a bottom wall 10*b*, a left wall 10*l* and a right wall 10*r*. The left wall 10*l* and the right wall 10*r* are denominated and illustrated with reference signs in accordance to FIG. 1 and FIG. 2.

The folding layer 12 includes a seam 13, which includes a middle section 13*m*, a left section 13*l*, and a right section 13*r*. The left section 13*l* and the right section 13*r* of the seam 13 are denominated and illustrated with reference signs in accordance to FIG. 1 and FIG. 2. The middle section 13*m* of the seam 13 connects together parts of the top wall 10*t* and the bottom wall 10*b*. The left section 13*l* of the seam 13 connects together parts of the left wall 10*l*, the top wall 10*t* and the bottom wall 10*b*. The right section 13*r* of the seam 13 connects together parts of the right wall 10*r*, the top wall 10*t* and the bottom wall 10*b*. On a side facing a plane defined by the right wall 10*r*, the folding layer 12 exhibits a curved surface 11. On a side facing a plane defined by the left wall 10*l*, the folding layer 12 exhibits also curved surface (not illustrated with a reference sign). Depending on the geometries, material properties, fill level, etc., the curved surface 11 may extend from the seam 13 to the rigid part 20.

Figure 4:
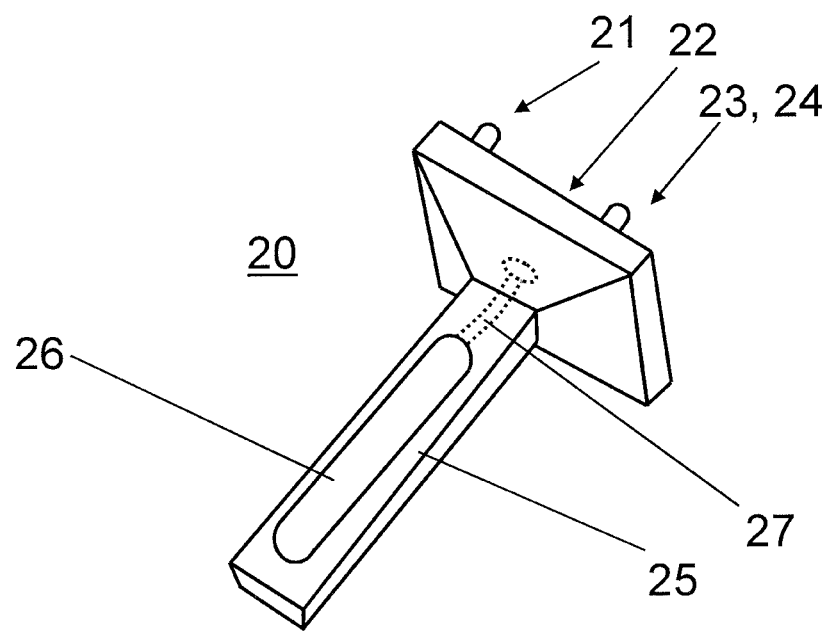
FIG. 4 a spatial view of the rigid part for a reservoir.

FIG. 4 illustrates a spatial view of the rigid part 20 for a reservoir 1. The rigid part 20 includes a support 25. The support 25 is connected to the rigid part 20. The rigid part 20 and the support 25 may be fabricated in the form of a single work piece. The support 25 supports the porous hydrophilic membrane 26. As indicated with reference signs, the rigid part 20 includes ports 21, 22 for enabling a fluidic access to the flexible container of the reservoir (not clearly visible in FIG. 4). As indicated with reference signs, the rigid part 20 includes pins 23, 24 for mounting the flexible reservoir to a medical device (not clearly visible in FIG. 4). As illustrated in FIG. 4, a fluidic connection 27 is arranged between the porous hydrophilic membrane 26 and a the port for delivery of the liquid medicament from the reservoir (not illustrated in FIG. 4).

Figure 5:
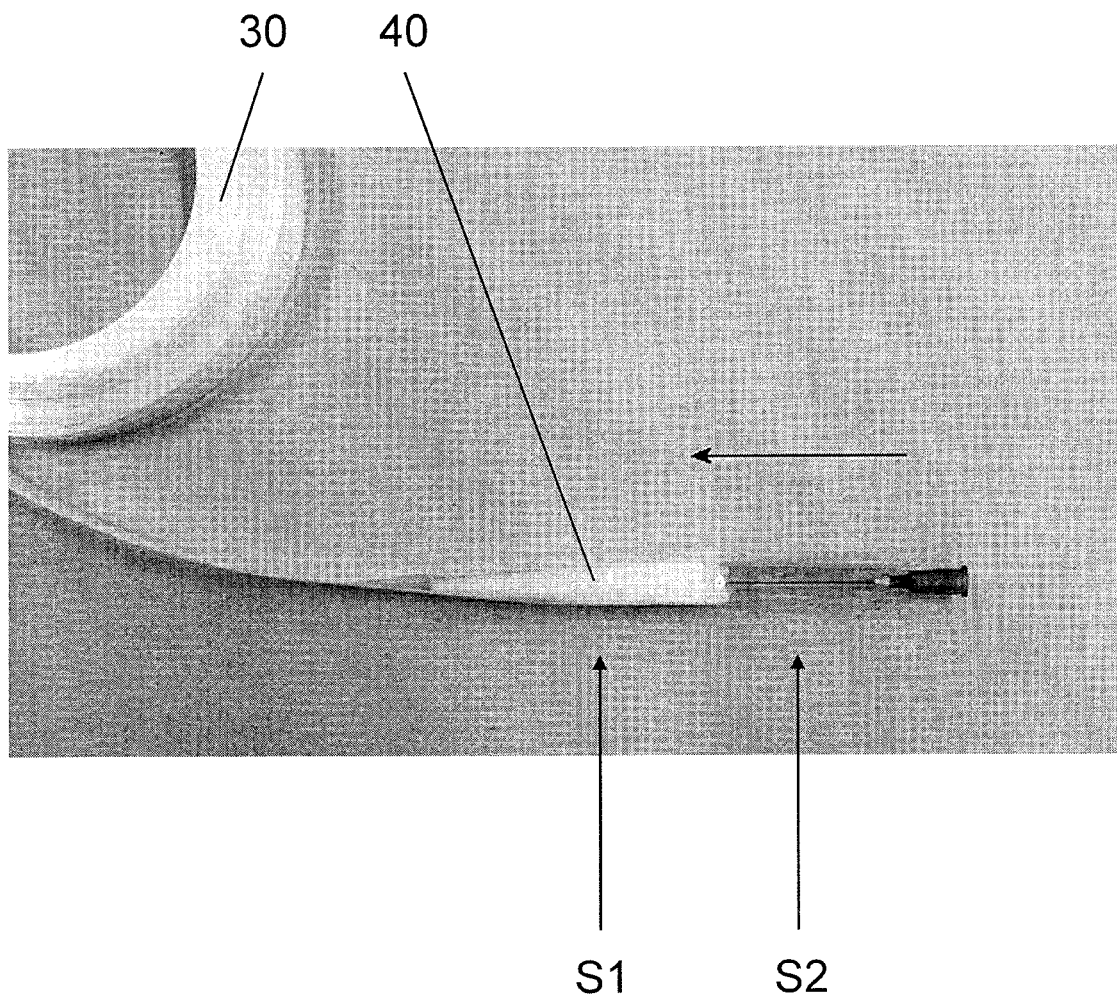
FIG. 5 a method for producing a reservoir.

FIG. 5 illustrates schematically a method for producing a reservoir 1.

The method for producing a reservoir 1 comprises providing a flexible tube 30 and a movable opening device 40 located inside the flexible tube 30. In some embodiments, the opening device 40 has the design of a cotter, a wedge, or a similar design. The opening device 40 provides that the flexible tube 30 can be brought from a folded state into an opened state, such that the rigid part 20 can be mounted into the flexible tube 30. The flexible tube 30 may be provided in the form of a roll, wherein an end of the flexible tube 30 is unrolled and wherein the moveable opening device 40 has been inserted through the end of the flexible tube 30 and is located inside the flexible tube 30. Along the movable opening device 40, towards the foil roll, the cross section of the flexible tube 30 has a flat shape and towards the end of the flexible tube 30 the cross section has a rectangular shape.

The method for producing a reservoir 1 comprises moving S1 the moveable opening device 40 inside the flexible tube 30. As illustrated in FIG. 5, the moveable opening device 40 is moved towards the foil roll. The moveable opening device 40 is moved a distance that enables production of the flexible container 10 in the following step. Between the moveable opening device 40 and the end of the flexible tube 30, the flexible tube 30 has the form of a cuboid.

The method for producing a reservoir 1 comprises providing a rigid part 20. The rigid part 20 may include a support 25 for supporting an porous hydrophilic membrane 26, as illustrated in FIG. 4. The support 25 and the porous hydrophilic membrane 26 may be inserted into the part of the flexible cube 30 that has the form of a cuboid, as described above.

The method for producing a reservoir 1 comprises bonding S2 the flexible tube 30 to the rigid part and providing a folding layer 12 included in the flexible container 10. A welding method may be applied that tightly bonds the foil to the rigid part 20 kitty-corner. A welding method may be applied that provides a seam 13 of the folding layer 12 included in the flexible container 10. The foil tube may be cut in order to provide a reservoir 1 as illustrated in FIGS. 1-3.

1 fluid reservoir
10 flexible container
10t top wall of the flexible container
10b bottom wall of the flexible container
10l left wall of the flexible container
10r right wall of the flexible container
11 curved surface
12 folding layer
13 seam
13l left section of the seam
13m middle section of the seam
13r right section of the seam
20 rigid part
21, 22 ports
23, 24 pins
25 support
26 porous hydrophilic membrane
27 fluidic connection
30 flexible tube
40 movable opening device

The invention claimed is:

1. A reservoir for storing a liquid medicament, comprising:
   a flexible container comprising a proximal end and a distal end, and further including side walls extending from the distal end and terminating at the proximal end, the side walls defining a proximal end opening, the flexible container comprising a folding layer terminating at the distal end in a seam which provides for a sealing of the flexible container,
   a rigid part connected to the side walls and enclosing the proximal end opening of the flexible container, the rigid part including one or more ports;
   a support connected to the rigid part and extending into the flexible container, the support including an opening in communication with the one or more ports and providing fluidic access to the interior of the flexible container, and
   a porous hydrophilic membrane connected to the support and covering the opening of the support,
   the reservoir having a first condition in which the folding layer is folded and a second condition in which the folding layer is unfolded.

2. The reservoir according to claim 1, wherein the flexible container includes four side walls defining a proximal rectangular end opening, the rigid part being rectangular and being received by and connected to the four side walls, the rigid part enclosing the proximal rectangular end opening, thereby sealing the proximal rectangular end opening.

3. The reservoir according to claim 2, wherein the flexible container includes a section of a foil tube, the section of the foil tube has a rectangular cross section defining the proximal rectangular end opening of the flexible container.

4. The reservoir according to claim 1, wherein the flexible container includes a section of a foil tube.

5. The reservoir according to claim 4, wherein the section of the foil tube has a folded cross section.

6. The reservoir according to claim 1, wherein the folding layer provides that walls of the flexible container exhibit a curved surface.

7. The reservoir according to claim 1, wherein the folding layer and the rigid part are arranged on opposite sides of the flexible container.

8. The reservoir according to claim 1, wherein the flexible container is bonded to the rigid part.

9. The reservoir according to claim 1, wherein the rigid part includes one or more mounting parts for mounting the reservoir to a medical device.

10. The reservoir according to claim 1, wherein the rigid part includes one or more pins for mounting the reservoir to a medical device.

11. A method for producing a reservoir comprising:
   providing a flexible tube and a movable opening device located inside the flexible tube,
   moving the movable opening device inside the flexible tube by a distance in a longitudinal direction of the flexible tube to provide a flexible container,
   forming a seam in the flexible tube to provide a sealed distal end of the flexible container,
   providing a folding layer in the flexible container adjacent the seam,
   removing the movable opening device from the flexible container to provide the flexible container with a proximal end, a distal end, and side walls extending from the distal end to terminate at the proximal end, and the side walls defining a proximal end opening,
   providing a rigid part, and
   bonding the side walls of the flexible container to the rigid part, thereby enclosing the proximal end opening.

12. The method according to claim 11, wherein the flexible tube and the rigid part are provided having a rectangular cross section enabling bonding of the flexible tube to the rigid part.

13. The method according to claim 11, wherein the flexible tube is a part of a foil tube and the forming the seam includes forming the seam and separating the flexible tube from the foil tube.

14. A method for filling a reservoir according to claim 1, comprising: actuating a fill device connected to the reservoir for filling the reservoir via the one or more ports at least partly with the liquid medicament thereby unfolding the flexible container.

15. A method for delivering a liquid medicament from a reservoir according to claim 1, comprising: actuating a delivery device connected to the reservoir for at least a partial delivery via the one or more ports of the liquid medicament stored in the reservoir and thereby folding the flexible container during the delivering.

16. A medical pump for an automated administration of a liquid medicament, wherein the medical pump comprises a reservoir according to claim 1.

* * * * *